(12) United States Patent
Chapman et al.

(10) Patent No.: US 12,362,064 B2
(45) Date of Patent: Jul. 15, 2025

(54) SYSTEMS ENABLING DOCTORS TO ACCESS MEDICAL DEVICE DATA

(71) Applicant: Physio-Control, Inc., Redmond, WA (US)

(72) Inventors: Fred W. Chapman, Newcastle, WA (US); Carrie Smith, Woodinville, WA (US); Kirill Ubozhenko, Kirkland, WA (US)

(*) Notice: Subject to any disclaimer, the term of this patent is extended or adjusted under 35 U.S.C. 154(b) by 680 days.

(21) Appl. No.: 17/495,745

(22) Filed: Oct. 6, 2021

(65) Prior Publication Data

US 2022/0108796 A1    Apr. 7, 2022

Related U.S. Application Data

(60) Provisional application No. 63/088,772, filed on Oct. 7, 2020.

(51) Int. Cl.
| | |
|---|---|
| *G16H 40/60* | (2018.01) |
| *A61B 5/00* | (2006.01) |
| *A61B 90/90* | (2016.01) |
| *G06F 21/62* | (2013.01) |
| *G16H 10/65* | (2018.01) |

(52) U.S. Cl.
CPC .............. *G16H 40/60* (2018.01); *A61B 5/681* (2013.01); *A61B 5/6833* (2013.01); *A61B 90/90* (2016.02); *G06F 21/6245* (2013.01); *G16H 10/65* (2018.01)

(58) Field of Classification Search
CPC ........ G16H 40/60; G16H 10/65; A61B 90/90; G06F 21/6245
See application file for complete search history.

(56) References Cited

U.S. PATENT DOCUMENTS

| | | | |
|---|---|---|---|
| 2003/0016122 A1* | 1/2003 | Petrick .................. | A61B 5/117 340/10.41 |
| 2014/0070012 A1* | 3/2014 | Hunt ...................... | G16Z 99/00 235/494 |
| 2014/0222095 A1* | 8/2014 | Einy ...................... | G16H 40/63 607/5 |

(Continued)

OTHER PUBLICATIONS

Giuseppe Ristagno et al., "Amplitude Spectrum Area to Guide Defibrillation: A Validation on 1617 Patients with Ventricular Fibrilation," Circulation, vol. 131, No. 5, Dec. 2, 2014.

(Continued)

*Primary Examiner* — Benjamin J Klein
*Assistant Examiner* — Thien Jason Tran

(57) ABSTRACT

An example method is performed by a defibrillator and includes obtaining event data regarding treatment provided to a patient. The method also includes obtaining a key that facilitates validating a request from a computing device to access the event data, associating the key with the event data, and transmitting the key and the event data to a server. Another example method is performed by a mobile device and includes obtaining an encoded version of an identifier of a medical device that is provided on the medical device. The medical device is configured to obtain event data regarding treatment provided to a patient. The method also includes obtaining a selection of a recipient for the event data, and causing a summary of the event data to be transmitted to the recipient.

19 Claims, 19 Drawing Sheets

(56) References Cited

U.S. PATENT DOCUMENTS

2017/0325091 A1\* 11/2017 Freeman ............ H04W 12/069
2019/0269914 A1\* 9/2019 Moaddeb ................ A61B 5/11
2020/0000679 A1\* 1/2020 Oppenheimer ...... A61N 1/3993

OTHER PUBLICATIONS

Paulien C.M. Homma et al., "Transfer of essential AED information to treating hospital (TREAT)," Resucitation vol. 149, Apr. 2020.
M. A. R. Bak et al., "Resucitation with an AED: putting the date to use," Netherlands Heart Journal vol. 29, Oct. 14, 2020.

\* cited by examiner

1300

```
┌─────────────────────────────────────────────────┐
│ OBTAINING, BY A DEFIBRILLATOR, EVENT DATA       │
│ REGARDING TREATMENT PROVIDED TO A PATIENT,      │
│ WHEREIN THE TREATMENT IS PROVIDED TO THE        │──1302
│ PATIENT WHILE THE DEFIBRILLATOR IS ATTACHED     │
│ TO THE PATIENT                                  │
└─────────────────────────────────────────────────┘
                        │
                        ▼
┌─────────────────────────────────────────────────┐
│ OBTAINING, BY THE DEFIBRILLATOR, A KEY THAT     │
│ FACILITATES VALIDATING A REQUEST FROM A         │──1304
│ COMPUTING SYSTEM TO ACCESS THE EVENT DATA       │
└─────────────────────────────────────────────────┘
                        │
                        ▼
┌─────────────────────────────────────────────────┐
│ ASSOCIATING, BY THE DEFIBRILLATOR, THE KEY      │──1306
│ WITH THE EVENT DATA                             │
└─────────────────────────────────────────────────┘
                        │
                        ▼
┌─────────────────────────────────────────────────┐
│ TRANSMITTING, BY THE DEFIBRILLATOR, THE KEY     │
│ AND THE EVENT DATA TO A SERVER IN A NETWORK     │──1308
│ FOR STORAGE                                     │
└─────────────────────────────────────────────────┘
```

```
┌─────────────────────────────────────────────────┐
│ OBTAINING, USING A COMPUTING SYSTEM, A KEY      │
│ ASSOCIATED WITH EVENT DATA REGARDING TREATMENT  │
│ PROVIDED TO A PATIENT USING A DEFIBRILLATOR,    │──1402
│ WHEREIN THE TREATMENT IS PROVIDED TO THE        │
│ PATIENT WHILE A DEFIBRILLATOR IS ATTACHED TO    │
│ THE PATIENT                                     │
└─────────────────────────────────────────────────┘
                        ↓
┌─────────────────────────────────────────────────┐
│ TRANSMITTING, BY THE COMPUTING SYSTEM, THE KEY  │──1404
│ TO A SERVER IN A NETWORK                        │
└─────────────────────────────────────────────────┘
                        ↓
┌─────────────────────────────────────────────────┐
│ RESPONSIVE TO TRANSMITTING THE KEY TO THE       │
│ SERVER, RECEIVING, BY THE COMPUTING SYSTEM FROM │──1406
│ THE SERVER, THE EVENT DATA ASSOCIATED WITH THE  │
│ KEY                                             │
└─────────────────────────────────────────────────┘
                        ↓
┌─────────────────────────────────────────────────┐
│ DISPLAYING, BY THE COMPUTING SYSTEM, A PORTION  │──1408
│ OF THE EVENT DATA                               │
└─────────────────────────────────────────────────┘
```

FIG. 14

SYSTEMS ENABLING DOCTORS TO ACCESS MEDICAL DEVICE DATA

CROSS-REFERENCE TO RELATED APPLICATIONS

The present application claims priority to U.S. provisional application No. 63/088,772, filed on Oct. 7, 2020, the entire contents of which are herein incorporated by reference.

BACKGROUND

During a cardiac arrest, a defibrillator, such as an automated external defibrillator (AED), can provide potentially lifesaving defibrillation treatment. For instance, a defibrillator is configured to supply a charge through the patient's heart via a set of defibrillation pads of a therapy cable. The defibrillation pads are located at a first end of the therapy cable and applied to chest of a patient. At a second end of the therapy cable, a connector couples the therapy cable to an electrical source of the defibrillator that is configured to generate a shock.

SUMMARY

Within examples described herein, systems and methods are described that allow medical professionals involved in treatment of a patient to access event data regarding previous treatment provided to the patient while a defibrillator was attached to the patient.

Within additional examples described herein, defibrillation pads are described that include mechanisms for imprinting a key on a patient's skin.

Within additional examples described herein, systems and methods are described that include causing a summary of event data regarding treatment provided to a patient to be transmitted to a selected recipient for the event data.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 13 shows a flowchart of an example of a method performed by a defibrillator, according to an example implementation.

FIG. 14 shows a flowchart of an example of a method performed by a computing system, according to an example implementation.

DETAILED DESCRIPTION

Figure 1:
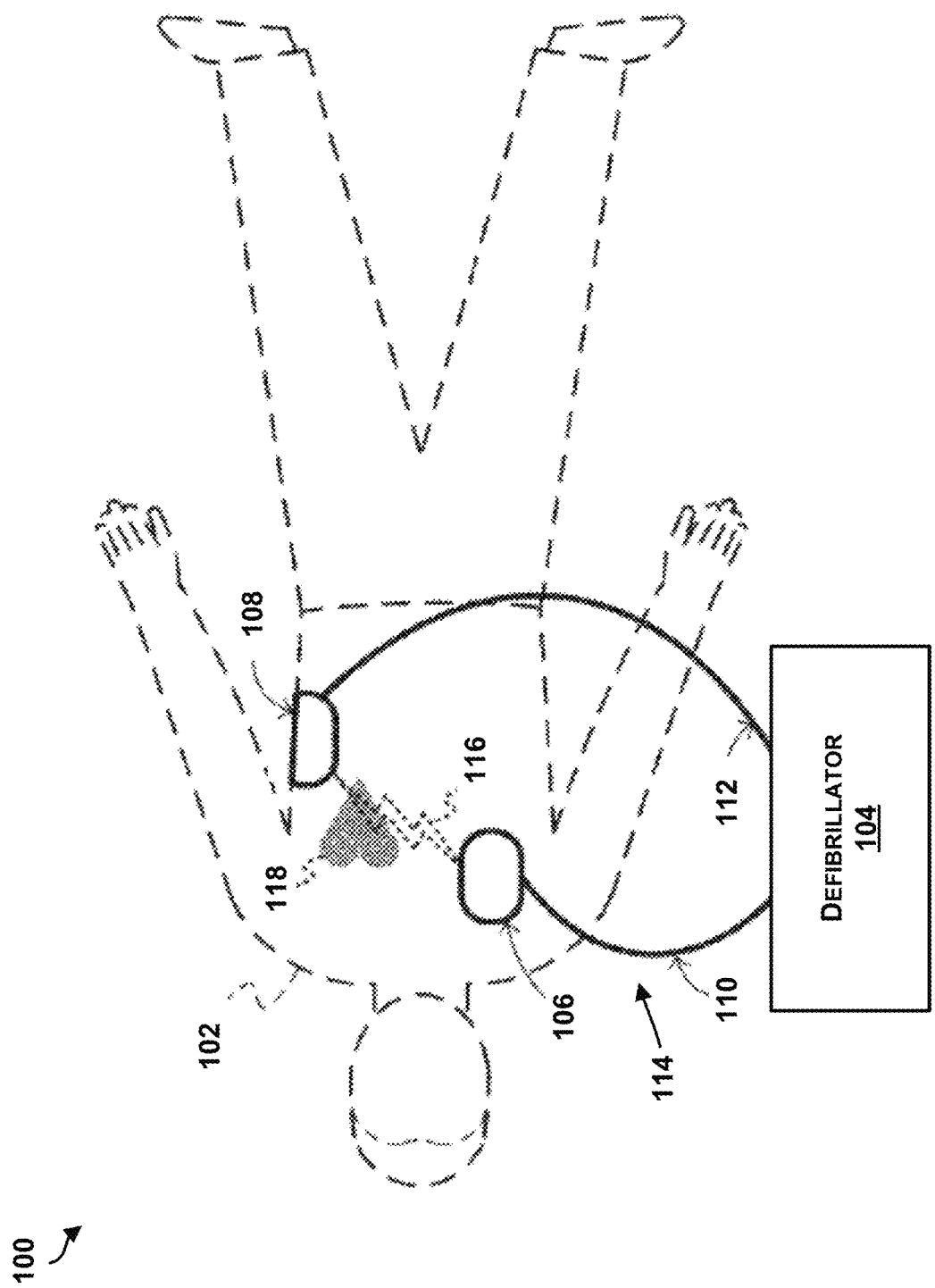
FIG. 1 illustrates an example defibrillation scene, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Currently, when a defibrillator, such as a public access defibrillator AED, is applied to a patient in cardiac arrest in the field, the defibrillator gathers data that can provide unique, valuable insight into the cause of the cardiac arrest. That information can help a physician in a hospital, minutes to hours later, when the physician is selecting a course of care for the patient. For example, if the physician in the hospital does not know that the patient had ventricular fibrillation (VF) and was defibrillated in the field, the patient can be discharged from the hospital without adequate measures to prevent or treat another episode of VF.

For several reasons, it is a common problem that such AED data might never make it to the physician, and that the patient therefore fails to receive appropriate care. Firstly, it is uncommon that the data from a public access defibrillator AED is downloaded at all, and even more uncommon that the data is provided promptly to medical professionals that need the data. Moreover, in one increasingly common scenario, soon after the cardiac arrest, a public access defibrillator AED is applied to the patient and delivers a shock. Thereafter, the patient resumes consciousness. When professional healthcare responders subsequently arrive, the responders discover an alert patient and sometimes fail to determine that a shock was delivered. Without that knowledge, the responders might not recognize that the patient is vulnerable to fibrillation and, when the responders transfer the patient to hospital staff, the responders might fail to provide that key information. As public access defibrillator AED use increases, these problems are becoming increasingly common.

Example methods and systems describe several ways that event data regarding treatment provided to a patient (e.g., while a defibrillator is attached to the patient) can be identified and accessed by a medical professional or other user. One example system includes a database residing on a server in a network. The database stores data from individual cases, with data for respective cases having an associated key. The key for a given case is assigned to the case during the initial treatment. That key then travels with the patient, and can subsequently be used to access the data for the patient's case from the database. Various techniques for assigning a key to a patient's case are described herein.

Additional example methods and systems describe techniques for causing a summary of event data regarding treatment provided to a patient to be transmitted to a selected recipient for the event data. For example, a mobile device can use an encoded version of an identifier of a medical device that is provided on the medical device to cause a summary of event data gathered by the medical device to be transmitted to a selected recipient. The mobile device can use a camera of the mobile device to obtain an image of a quick-response (QR) code provided on the medical device.

In some examples, the medical device is configured to obtain event data regarding treatment provided to a patient, and transmit the event data to a server. The mobile device can cause a summary of the event data to be transmitted to the selected recipient by transmitting a request to the server, with the request including an indication of the recipient and the identifier of the medical device. Reception of the request by the server can then cause the server to generate the summary of the event data and transmit the summary of the event data to the recipient. Alternatively, the mobile device can use the identifier of the medical device to obtain the event data from the server. After obtaining the event data, the mobile device can then generate the summary of the event data, and transmit the summary of the event data to the recipient.

Further details and features of these methods and systems are described hereinafter with reference to the figures.

Referring now to the figures, FIG. 1 illustrates an example defibrillation scene 100. As shown in FIG. 1, a patient 102 is lying on their back. Patient 102 could be a patient in a public space, a home, a pre-hospital environment, or even a hospital. A defibrillator 104 is currently being used to treat patient 102. As shown in FIG. 1, defibrillation pads 106, 108 of defibrillator 104 are applied to a chest of patient 102. Defibrillation pad 106 is coupled to defibrillator 104 via an electrode lead 110. Defibrillation pad 108 is coupled to defibrillator 104 via an electrode lead 112. Defibrillation pads 106, 108 and electrode leads 110, 112 are collectively referred to as a therapy cable 114. Defibrillator 104 can be used to deliver, via therapy cable 114, a shock 116. Shock 116 can go through a heart 118 of patient 102, in an attempt to restart heart 118, for saving the life of patient 102.

Defibrillator 104 can be one of multiple different types, each with different sets of features and capabilities. As one example, defibrillator 104 can be an AED, such as a public access defibrillator AED. An AED can make a decision as to whether or not to deliver a shock to a patient automatically. For example, an AED can sense physiological conditions, such as shockable heart rhythms, of a patient via defibrillation pads applied to the patient, and make the decision based on an analysis of the patient's heart. Further, an AED can either deliver the shock automatically, or instruct a user to deliver a shock, e.g., by pushing a button. AEDs can be operated by medical professionals as well as people who are not in the medical profession, such as policemen, firemen, or even a person with first-aid and CPR/AED training. AEDs can be located in public spaces or homes so that lifesaving treatment can hopefully be initiated before medical professionals arrive.

As another example, defibrillator 104 can be a more advanced device, such as a monitor defibrillator. Monitor defibrillators are intended to be used by trained medical professionals, such as doctors, nurses, paramedics, emergency medical technicians, etc. As the name suggests, a monitor defibrillator is a combination of a monitor and a defibrillator. As a defibrillator, a monitor defibrillator can be one of different varieties, or even versatile enough to be able to switch among different modes that individually correspond to the varieties. One variety is that of an automated defibrillator, which can determine whether a shock is needed and, if so, charge to a predetermined energy level and instruct the user to deliver the shock. Another variety is that of a manual defibrillator, where the user determines the need and controls delivery of the shock. As a patient monitor, the monitor defibrillator has features additional to what is needed for operation as a defibrillator. These features can be for monitoring physiological indicators of a patient in an emergency scenario, for instance.

Figure 2:
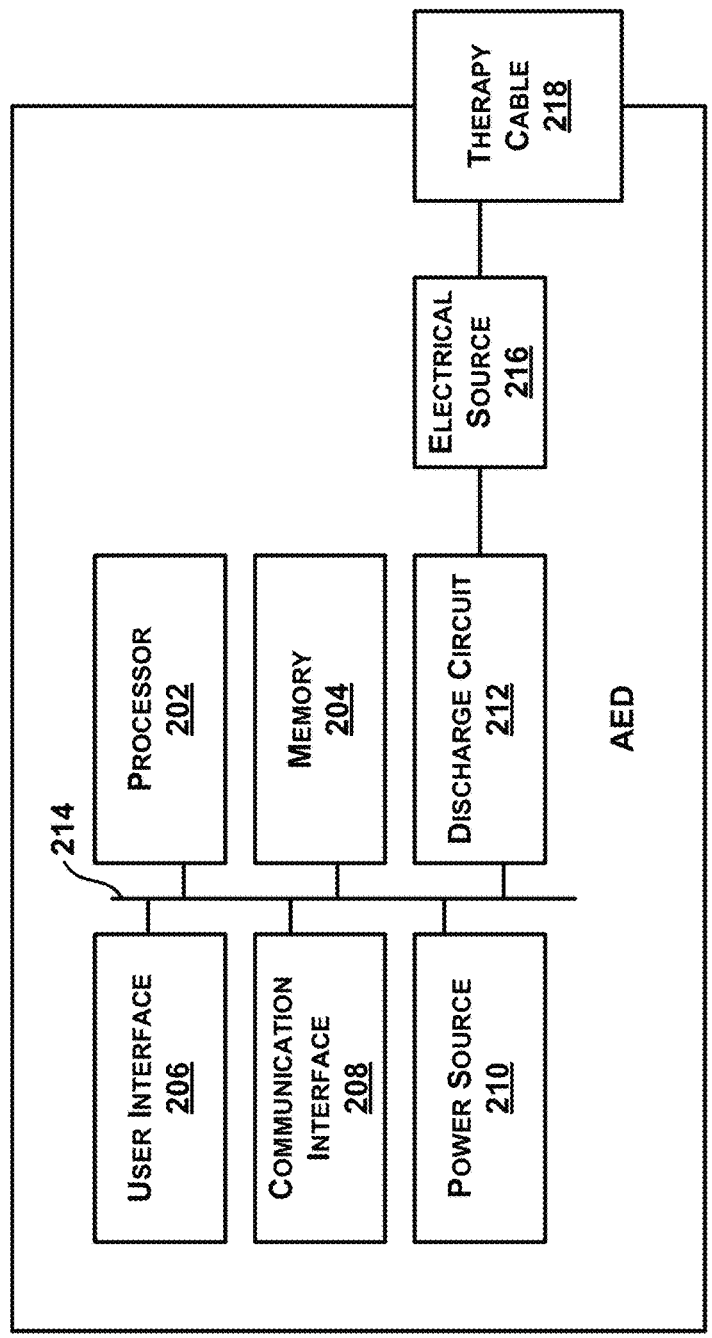
FIG. 2 illustrates a block diagram of an example defibrillator, according to an example implementation.

FIG. 2 illustrates an example AED 200. In FIG. 2, AED 200 includes a processor 202, a memory 204, a user interface 206, a communication interface 208, a power source 210, and a discharge circuit 212, each connected to a communication bus 214. AED 200 also includes an electrical source 216 connected to discharge circuit 212, and a therapy cable 218 connected to electrical source 216.

Memory 204 may include one or more computer-readable storage media that can be read or accessed by processor 202. The computer-readable storage media can include volatile and/or non-volatile storage components, such as optical, magnetic, organic or other memory or disc storage, which can be integrated in whole or in part with processor 202. The non-transitory data storage is considered non-transitory computer readable media. In some examples, the non-transitory data storage can be implemented using a single physical device (e.g., one optical, magnetic, organic or other memory or disc storage unit), while in other examples, the non-transitory data storage can be implemented using two or more physical devices.

The non-transitory data storage thus is a computer readable medium, and instructions are stored thereon. The instructions include computer executable code.

Processor 202 may be a general-purpose processor or a special purpose processor (e.g., digital signal processor, application specific integrated circuit, etc.). Processor 202 may receive inputs from other components of AED 200 and process the inputs to generate outputs that are stored in the non-transitory data storage. Processor 202 can be configured to execute instructions (e.g., computer-readable program instructions) that are stored in the non-transitory data storage and are executable to provide the functionality of the AED described herein.

User interface 206 can take any of a number of forms. For example, user interface 206 may include output devices, which can be visual, audible or tactile, for communicating to a user. An output device can be configured to output a warning, which warns or instructs the patient or a bystander to do something. An output device can be a light or a screen to display what is detected and measured, and provide visual feedback to the rescuer for their resuscitation attempts. User interface 206 may also include a speaker, to issue voice prompts or sounds. User interface 206 may also include a printer configured to print data on a piece of paper. User interface 206 may additionally include input devices for receiving inputs from users. Such input devices may include various controls, such as pushbuttons, keyboards, touchscreens, a microphone, a fingerprint scanner, a retinal scanner, and/or a camera.

Communication interface 208 may be one or more wireless interfaces and/or one or more wireline interfaces that allow for both short-range communication and long-range communication to one or more networks or to one or more remote devices. Such wireless interfaces may provide for communication under one or more wireless communication protocols, such as Bluetooth, Wi-Fi (e.g., an institute of electrical and electronic engineers (IEEE) 802.11 protocol), Long-Term Evolution (LTE), cellular communications, near-field communication (NFC), radio-frequency identification (RFID), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Communication interface 208 thus may include hardware to enable communication between AED 200 and other devices (not shown). The hardware may include transmitters, receivers, and antennas, for example.

Power source 210 may include battery power, or a wired power means such as an AC power connection.

Electrical source 216 can be configured to store electrical energy in the form of an electrical charge, when preparing for delivery of a shock. Discharge circuit 212 can be controlled to permit the energy stored in electrical source 216 to be discharged to defibrillation pads of therapy cable 218. Discharge circuit 212 can include one or more switches, such as an H-bridge. Processor 202 can instruct discharge circuit 212 to output a shock using one of various energy levels. The energy levels can range from 50 Joules to 360 Joules. For instance, for an adult, processor 202 can select an energy level from an adult energy sequence that includes energy levels of 200 Joules, 300 Joules, and 360 Joules. Whereas, for a pediatric patient, processor 202 can select an energy level from a pediatric energy sequence that includes energy levels of 50 Joules, 75 Joules, and 90 Joules.

Therapy cable 218 can be detachable from a housing of AED 200 by way of a connector. The connector can be a tabbed, male connector that is compatible with a port of AED 200. The defibrillation pads of therapy cable 218 can be similar to defibrillation pads 106, 108 of FIG. 1. The defibrillation pads can include sensors that output physiologic monitoring data measurements to processor 202. For example, the defibrillation pads can include sensors that measure heart electrical activity such as electrocardiogram (ECG).

After a shock is delivered, or in parallel with the instructing of discharge circuit 212 to deliver a shock, processor 202 can store data indicative of the shock in memory 204. The data indicative of the shock can include one or any combination of an energy level of the shock, a timestamp associated with the shock, an identification of AED 200, such as a model number or serial number of AED 200, an indication of a number of the shock (e.g., an indication that the shock is the first shock, second, shock, third shock, etc.), and an error code associated with the shock.

Additionally or alternatively, during a patient care event, processor 202 can determine and store other data in memory 204. As one example, processor 202 can determine and store data indicating that return of spontaneous circulation (ROSC) was achieved after delivering a shock. Processor 202 could determine that ROSC was achieved using one or more of the following techniques: inferring that ROSC was achieved via electrical signals; detecting a motion artifact that does not correspond to compressions or moving a patient; determining whether a trend after serval complete PQRST waveforms shows degradation; identifying respiratory breath from ECG; receiving information (e.g., wirelessly) from an accessory configured to deliver information to AED 200, such as blood pressure, SpO2, CO2, etc.; voice recognition that identifies keywords such as "I feel a pulse!". Processor 202 can also determine that ROSC was achieved after delivering a shock based on receiving an indication from another device. For instance, processor 202 can send data obtained by AED 200 to a server in network. The server, in turn, can analyze the data to determine whether or not the data is indicative of ROSC being achieved (e.g., using any of the techniques noted above), and send to AED 200 data indicative of whether or not ROSC was achieved.

As another example, processor 202 can analyze ECG data, determine a fibrillation type using the ECG data, and store an indication of the fibrillation type. Ventricular fibrillation (VF) can be qualified as either refractory VF or recurrent VF. Refractory VF refers to VF that persists despite shock delivery. This is in contrast to recurrent VF, which is VF that re-appears after it had previously been terminated. The indication of fibrillation type could therefore include an indication of refractory VF or an indication of recurrent VF. Similarly, processor 202 can analyze ECG data, determine a coarseness of a VF waveform, and store an indication of the coarseness of the VF waveform. As still another example, processor 202 can store an initial rhythm measured by AED 200, such as a few seconds of raw ECG data that is obtained before delivery of any shocks. Processor 202 can also determine and store data indicative of an algorithm used to measure the initial rhythm, such as data indicative of a name of the algorithm. In some examples, processors 202 can analyze ECG data and determine an amplitude spectrum area (AMSA) using the ECG data.

As yet another example, processor 202 can determine whether CPR is being performed, and then store in memory 204 data indicative of whether or not CPR was performed on the patient. For example, processor 202 can determine whether CPR is being performed based on analysis of impedance signals received from the defibrillation pads of therapy cable 218. As another example, processor 202 can determine whether CPR is being performed based on an analysis of an ECG signal. CPR results in a very rhythmic change in ECG signal. Processor 202 can detect such a change using signal processing. Such processing can involve providing the ECG signal to a trained neural network that is configured to output an indication of whether the ECG signal is indicative of CPR being performed. The neural network can be trained using ECG signals that are known to have been captured while CPR is being performed. The data indicative of whether or not CPR was performed can include data for individual compressions (e.g., compression rate data). Additionally or alternatively, the data indicative of whether or not CPR was performed can include a binary indication (e.g., yes or no), or a qualitative indication (e.g., no CPR; bad CPR; moderate CPR; good CPR; great CPR). Processor 202 can also determine and store in memory 204 and/or memory 220 data indicative of whether or not AED 200 advised a user to continue CPR after a shock was delivered.

As yet another example, processor 202 can determine and then store in memory 204 data indicative of whether any noise was detected during the patient care event. Examples of noise include motion of the patient (e.g., chest compressions performed during analysis of the patient's heart), the presence of an additional defibrillator attached to the patient, detection of a pacemaker or other implantable device. In one example, processor 202 can detect such noise through signal processing of an ECG signal. Such signal processing can include performing a Fourier transform, and analyzing the resulting frequency information. For instance, implanted electrical signal stimulator usually pulse very rhythmically and, as a result, may be detectable from a Fourier transform of an ECG signal.

Further, during or after the treatment is provided, AED 200 can upload to a database event data regarding treatment provided to a patient. For instance, AED 200 can use communication interface 208 to transmit any of the data stored in memory 204 to a server, and the server can store the event data in a database. Optionally, the server can analyze the event data and determine additional information. For instance, the server can perform any of the analysis processes mentioned above, such as analyzing ECG data to identify one or more rhythms (e.g., VF), determine an AMSA, or detect a segment during which CPR is not being performed.

Figure 3:
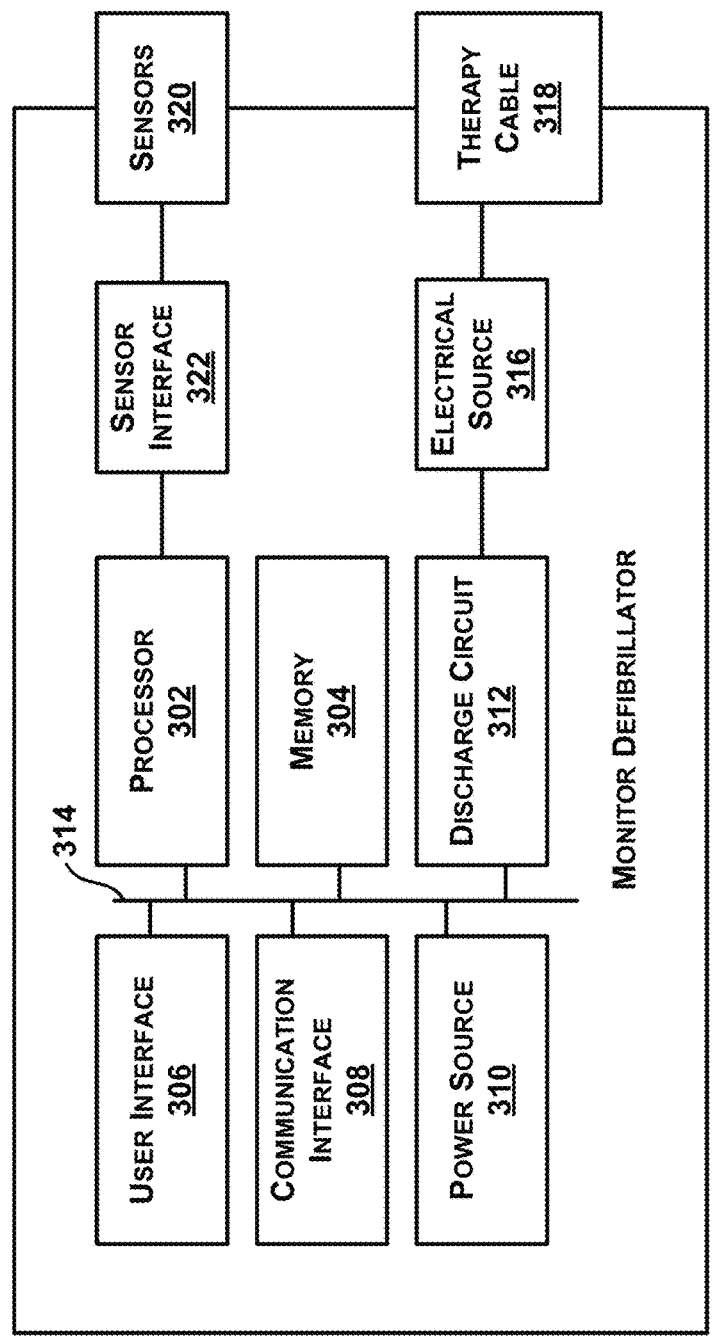
FIG. 3 illustrates a block diagram of another example defibrillator, according to an example implementation.

FIG. 3 illustrates an example monitor defibrillator 300. Like AED 200 of FIG. 2, monitor defibrillator 300 includes a processor 302, a memory 304, a user interface 306, a communication interface 308, a power source 310, and a discharge circuit 312, each connected to a communication bus 314. Monitor defibrillator 300 also includes an electrical source 316 connected to discharge circuit 312, and a therapy cable 318 connected to electrical source 316.

Unlike AED 200, monitor defibrillator 300 includes physiologic monitoring sensors 320 and a sensor interface 322 that couples physiologic monitoring sensors 320 with processor 302. Physiologic monitoring sensors 320 allow for monitoring physiological indicators of a patient. Any number or type of sensors may be used depending on treatment or monitoring of the patient. In many instances, a variety of sensors are used to determine a variety of physiologic monitoring data. Physiologic monitoring data can include vital sign data (e.g., heart rate, respiration rate, blood pressure, and body temperature), as well as signals from other sensors described herein. In addition, physiologic monitoring data can also include treatment monitoring data, such as location at which an endotracheal tube has been placed or other sensor context information. The physiologic monitoring data can include timestamps associated with a time of collection and may be considered a measurement at a specific time. In some instances herein, physiologic monitoring data refers to one measurement and data associated with the one measurement, and in other instances, physiologic monitoring data refers to a collection of measurements as context indicates.

Physiologic monitoring sensors 320 can include sensors that measure heart electrical activity such as electrocardiogram (ECG), saturation of the hemoglobin in arterial blood with oxygen (SpO2), carbon monoxide (carboxyhemoglobin, COHb) and/or methemoglobin (SpMet), partial pressure of carbon dioxide (CO2) in gases in the airway by means of capnography, total air pressure in the airway, flow rate or volume of air moving in and out of the airway, blood flow, blood pressure such as non-invasive blood pressure (NIBP) or invasive blood pressure (IP) by means of a catheter, core body temperature with a temperature probe in the esophagus, oxygenation of hemoglobin within a volume of tissue (rSO2), indicating level of tissue perfusion with blood and supply of oxygen provided by that perfusion, and so forth.

Outputs, e.g., signals, from physiologic monitoring sensors 320 are conveyed to processor 302 by way of sensor interface 322. Processor 302 records the signals and uses the signals for vital sign qualification and caregiver feedback. In some examples, outputs from physiologic monitoring sensors 320 or data derived from an analysis of the outputs can be recorded in a patient care record of monitor defibrillator 300 and delivered to subsequent entities (e.g., hospital emergency department, etc.) via communication interface 308.

Like AED 200 of FIG. 2, during or after treatment is provided by monitor defibrillator 300, monitor defibrillator 300 can upload to a database event data regarding treatment provided to a patient. For instance, monitor defibrillator 300 can use communication interface 308 to transmit any of the data stored in memory 304 to a server, and the server can store the event data in a database.

Figure 4:
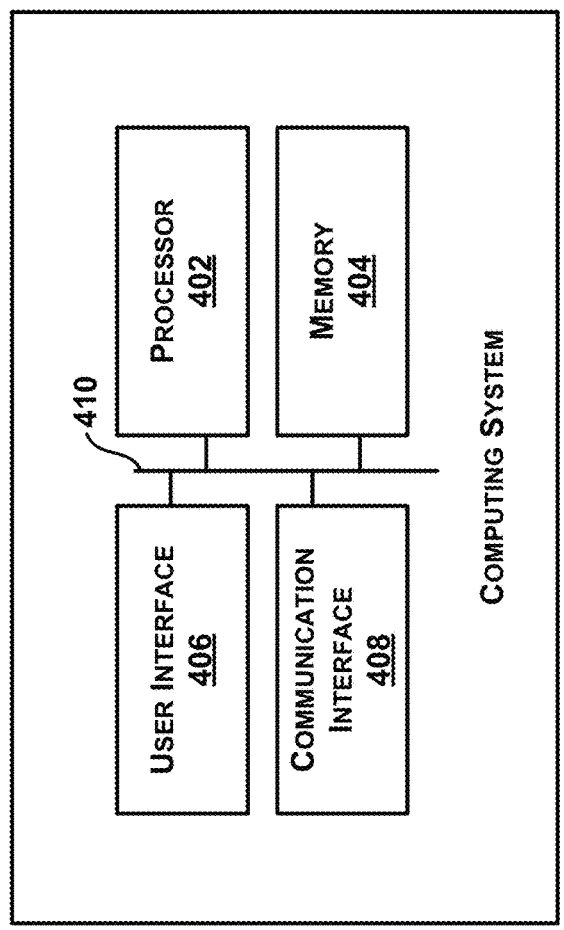
FIG. 4 illustrates a block diagram of an example computing system, according to an example implementation.

FIG. 4 illustrates an example computing system 400. Computing system 400 can perform various acts and/or functions, such as those described in this disclosure. Computing system 400 can include various components, such as processor 402, memory 404, communication interface 406, and/or user interface 408. These components can be connected to each other (or to another device, system, or other entity) via connection mechanism 410.

Processor 402 can include a general-purpose processor (e.g., a microprocessor) and/or a special-purpose processor (e.g., a digital signal processor (DSP)).

Memory 404 can include one or more volatile, non-volatile, removable, and/or non-removable storage components, such as magnetic, optical, or flash storage, and/or can be integrated in whole or in part with processor 402. Further, memory 404 can take the form of a non-transitory computer-readable storage medium, having stored thereon program instructions (e.g., compiled or non-compiled program logic and/or machine code) that, when executed by processor 402, cause computing system 400 to perform one or more acts and/or functions, such as those described in this disclosure. As such, computing system 400 can be configured to perform one or more acts and/or functions, such as those described in this disclosure. Such program instructions can define and/or be part of a discrete software application. In some instances, computing system 400 can execute program instructions in response to receiving an input, such as from communication interface 406 and/or user interface 408. Memory 404 can also store other types of data, such as those types described in this disclosure.

Communication interface 406 can allow computing system 400 to connect to and/or communicate with another other entity according to one or more protocols. In one example, communication interface 406 can be a wired interface, such as an Ethernet interface or a high-definition serial-digital-interface (HD-SDI). In another example, communication interface 406 can be a wireless interface, such as a cellular, WI-FI, RFID, and/or NFC interface. In this disclosure, a connection can be a direct connection or an indirect connection, the latter being a connection that passes through and/or traverses one or more entities, such as such as a router, switcher, or other network device. Likewise, in this disclosure, a transmission can be a direct transmission or an indirect transmission.

User interface 408 can facilitate interaction between computing system 400 and a user of computing system 400, if applicable. As such, user interface 408 can include input components such as a keyboard, a keypad, a mouse, a touch-sensitive panel, a microphone, a camera, a fingerprint scanner, and/or a retinal scanner, and/or output components such as a display device (which, for example, can be combined with a touch-sensitive panel), a sound speaker, and/or a haptic feedback system. More generally, user interface 408 can include hardware and/or software components that facilitate interaction between computing system 400 and the user of the computing system 400.

Computing system 400 can take various forms, such as a workstation terminal, a desktop computer, or a mobile device. Examples of mobile devices include a mobile phone, a laptop, a tablet, or a wearable computing device.

Figure 5:
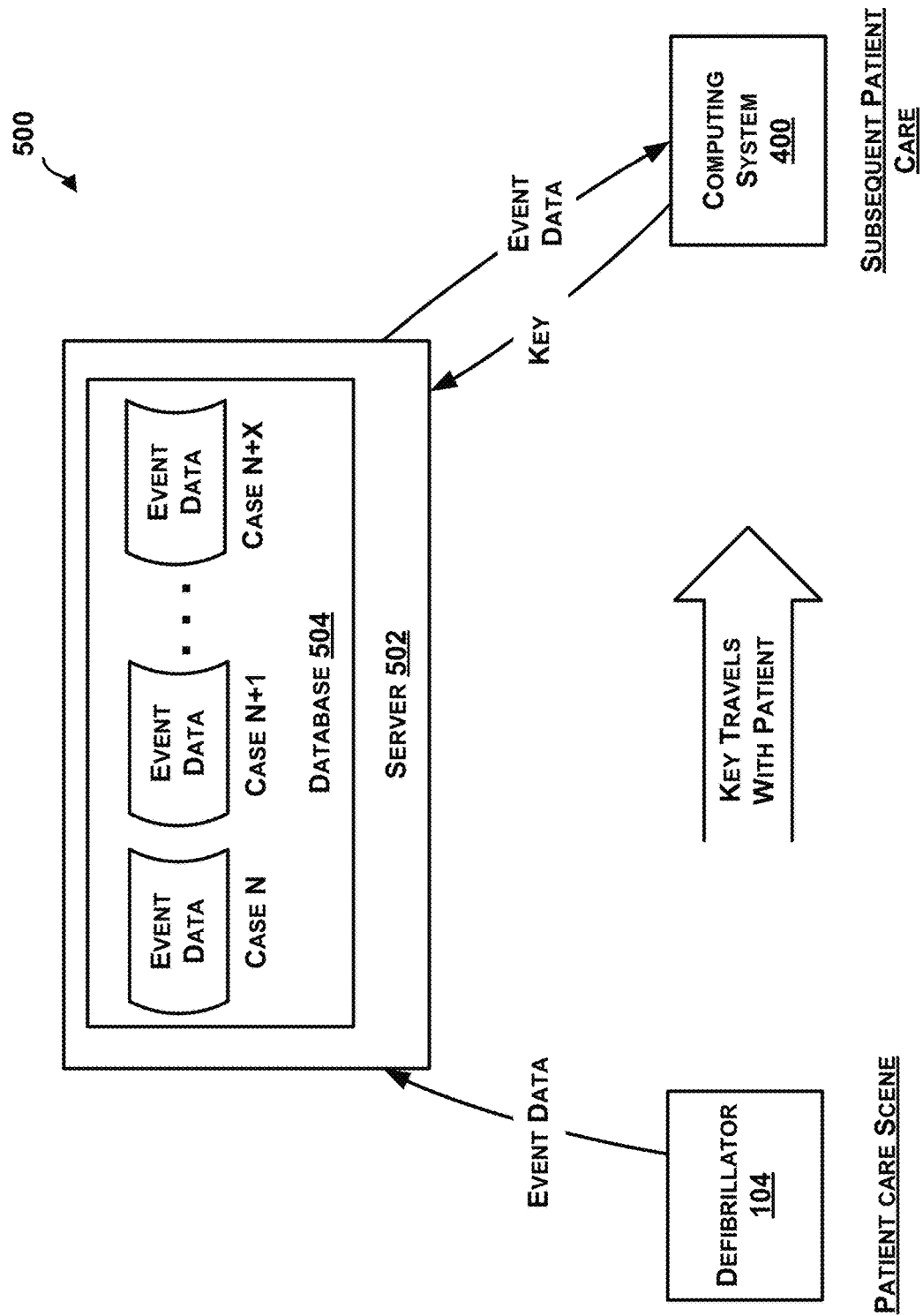
FIG. 5 illustrates an example system, according to an example implementation.

FIG. 5 illustrates an example system 500. In line with the discussion above, system 500 allows medical professionals or other users to identify and access event data regarding treatment provided to a patient. As shown in FIG. 5, system 500 includes defibrillator 104, computing system 400, and a server 502. Server 502, in turn, includes a database 504 storing event data from individual cases. Event data for an individual case is received from a defibrillator, such as defibrillator 104. In addition, event data is accessible using a respective key. The key for an individual case is assigned to the individual case during a patient care event. The key is then associated with event data for the individual case. In addition, that key then travels with the patient after the patient leaves the patient care scene, and can subsequently be used to unlock and retrieve the event data for the patient's case. For instance, computing system 400 can obtain the key that travels with the patient, and use the key to retrieve the event data from database 504.

A key can be associated with a patient's case in several ways. As one example, defibrillator 104 can associate a key with a patient's case using a near-field communication (NFC) chip. For instance, defibrillator 104 can be equipped for future use by connecting it to a disposable cartridge that includes a set of defibrillation pads. Packaged in the cartridge with those defibrillator pads, and in close proximity to a chassis of defibrillator 104 by virtue of the physical design, is a passive NFC chip. The NFC chip can be embedded within a bracelet or badge that is attachable to the patient. Further, defibrillator 104 includes an active NFC chip connected to a processor of defibrillator 104.

During a patient care event, when defibrillator 104 is powered on, defibrillator 104 can use the active NFC chip to wirelessly transmit a key to the passive NFC chip included within the disposable cartridge. The key can include a number generated by defibrillator 104, such as a randomly generated number. In some examples, defibrillator 104 refrains from writing the key to the passive NFC chip until defibrillator 104 senses that defibrillation pads have been attached to the patient. Defibrillator 104 can determine whether or not the defibrillation pads are attached by sensing impedance using sensors of the defibrillation pads. Alternatively, during the patient care event, defibrillator 104 can use the active NFC chip to read a key from the passive NFC chip.

Further, during the patient care event, following voice prompts issued by defibrillator 104, an operator can open the disposable cartridge and apply the defibrillation pads to the patient. In addition, the operator can apply cardiopulmonary resuscitation (CPR) to the patient and/or deliver one or more shocks. In line with the discussion above, defibrillator 104 can gather event data while defibrillator 104 is attached to the patient. Optionally, defibrillator 104 can write a portion or summary of the event data to the passive NFC chip.

At some point during use of defibrillator 104, such as when the defibrillation pads are detached from the patient or when the defibrillation pads are disconnected from defibrillator 104, voice prompts from defibrillator 104 instruct the operator to remove a bracelet having the embedded NFC chip from the disposable cartridge and place it on the patient's wrist or ankle. Alternatively, the voice prompts from defibrillator 104 can instruct the operator to remove a badge having the embedded NFC chip from the disposable cartridge and adhere the badge to a visible location on the patient (e.g., stick the badge to a patient's chest or forearm). In some instances, defibrillator 104 can continue to issue such voice prompts until the active NFC chip of defibrillator 104 no longer detects the presence of the passive NFC chip, indicating that the passive NFC chip has been removed from the disposable cartridge.

Either during the patient care event, at the end of the patient care event, or at later time when defibrillator 104 establishes a connection to server 502, defibrillator 104 transmits event data and the key to server 502. Server 502 then uses the key to validate requests for access to the event data. For example, in order to access event data, computing system 400 provides the key to server 502. Server 502 then determines whether database 504 includes any event data associated with the received key. If so, server 502 transmits the event data associated with the received key to computing system 400.

In some examples, server 502 also uses a second level of validation when responding to requests for event data. For instance, a user of computing system 400 can provide credentials proving that the user is a licensed healthcare provider. Computing system 400 can send the credentials to server 502 (or another server) to verify the credentials. The verifying of credentials can occur in an automated manner (e.g., by cross-checking information with a database), or through interaction with a customer service representative. After the credentials are verified, computing system 400 can then request event data form server 502. Based on the credentials of the user of the computing system 400 having been verified, server 502 can then respond to the request for event data.

In some examples, server 502 can apply analytics to the event data to derive useful summary information from the event data. The summary information can include a detected rhythm(s) or AMSA determined using ECG data, for instance. The summary information can also include a segment of ECG data that is annotated as being ECG data that corresponds to a time when CPR was not being performed.

Later in the course of care of the patient, such as a few hours or days later, a medical professional can use computing system 400 to read the key from the NFC chip embedded within the bracelet or badge. The bracelet or badge might still be attached to the patient at this time. For instance, computing system 400 can be a mobile device having an NFC device that is configured to read NFC chips. Optionally, computing system 400 can read a portion or summary of the event data from the NFC chip embedded within the bracelet or badge.

Alternatively, instead of using NFC technology to associate a key with a patient, defibrillator 104 can use radio-frequency identification (RFID) technology to associate a key with a patient. With this approach, the bracelet or badge packaged within the disposable cartridge can include an embedded RFID tag that stores a key. At the patient care scene, defibrillator 104 can read the key using an RFID reader. Similarly, during subsequent patient care, computing system 400 can read the key using an RFID reader.

Defibrillator 104 can also use a quick response (QR) code to associate a key with a patient's case. For instance, a bracelet or badge packaged within the disposable cartridge can include a QR code printed on the bracelet or badge. The QR code can encode a key. Defibrillator 104 can determine the key by reading the QR code with a QR code reader when defibrillator is being prepared for future use. Alternatively, defibrillator 104 can determine the key by accessing configuration information that is programmed for defibrillator 104 prior to use of defibrillator 104. For instance, a user can use a user interface of defibrillator 104 or a defibrillator configuration program accessible to a system administrator to provide the key. The key could be printed on packaging for the disposable cartridge, such that the user could read the key and then program the configuration information. Or a user can insert a memory card into defibrillator 104, with the memory card storing the key, and defibrillator 104 can read the memory card to determine the key. During subsequent patient care, computing system 400 can determine the key by reading the QR code using a QR code reader.

In some examples, a badge or bracelet might not be able to wirelessly communicate with defibrillator 104. For instance, a badge or bracelet might have a memory card. While the badge or bracelet is packaged within the disposable cartridge, the memory card can be communicatively coupled to defibrillator 104 using a wired connection. During the patient care event, defibrillator 104 can write a key to the memory card. Optionally, defibrillator 104 can also write the event data gathered by defibrillator 104, or a summary or portion of the event data, to the memory card. After use of defibrillator 104 ends, defibrillator 104 may prompt a user (e.g., by way of voice prompts) to remove the bracelet or badge and apply the bracelet or badge to the patient.

During subsequent patient care, computing system 400 can read the key from the memory card, and use the key to access the event data from server 502. Additionally or alternatively, if the memory card also includes event data, the computing system 400 can also read the event data from the memory card. In some instances, the memory card can be a removable memory card. In other instances, the bracelet or badge can include a communication port that facilitates transferring data from the memory card to computing system using a data cable.

Further, in some examples, the bracelet can be designed such that access to the memory card of the bracelet or badge is not possible without cutting the bracelet off the patient. For instance, the memory card might only be removable from an inner side of the bracelet, such that while the bracelet is being worn, the memory card cannot be removed.

In some examples, the bracelet or badge can display a timer that is indicative of a time that treatment is provided to the patient, such as a time that the bracelet or badge is removed from the disposable cartridge or a time that the defibrillator is powered on. With one approach, the bracelet or badge can include an insulating strip that is positioned between one side of a battery and a portion of a timer circuit. Removal of the insulating strip can cause the timer to begin. The insulating strip might be attached to the disposable cartridge, such that removal of the bracelet or badge from the disposable cartridge causes the insulating strip to be removed from the bracelet or badge and the timer to start. With another approach, the timer can be configured to begin in response to receiving a communication signal from defibrillator 104. For instance, defibrillator 104 can send the communication signal to the bracelet or badge when defibrillator 104 is powered on.

Figure 6:
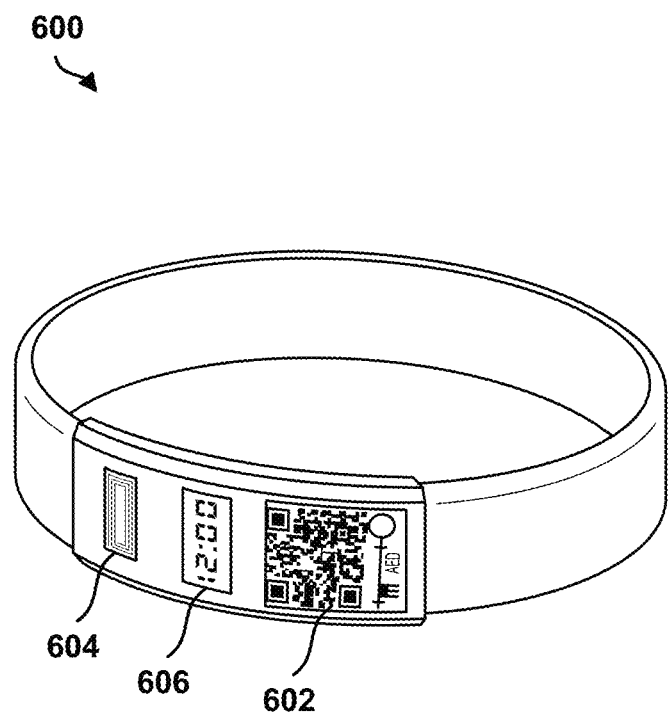
FIG. 6 illustrates an example bracelet, according to an example implementation.
Figure 7:
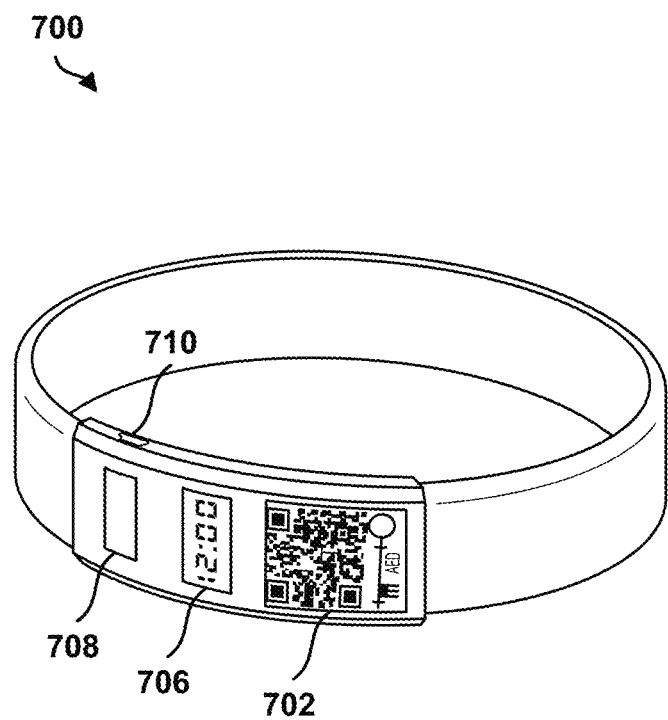
FIG. 7 illustrates another example bracelet, according to an example implementation.

FIGS. 6 and 7 illustrate example bracelets 600, 700 that can be included within a disposable cartridge for a defibrillator. As shown in FIG. 6, bracelet 600 includes a QR code 602, a communication device 604, and a timer 606. In line with the discussion above, communication device 604 can include a NFC chip or an RFID tag.

As shown in FIG. 7, bracelet 700 similarly includes a QR code 702 and a timer 706. However, unlike bracelet 600 of FIG. 6, bracelet 700 includes a memory card 708 and a communication port 710. A computing system, such as computing system 400 of FIG. 5, can read data from memory card 708 by connecting a data cable to communication port 710. Alternatively, a user can remove memory card 708 from bracelet 700 and insert memory card 708 into a memory card reader of a computing system to read data from memory card 708.

Bracelet 600 or bracelet 700 can be packaged within a cartridge for a defibrillator. For instance, a cartridge can include a first defibrillation pad, a second defibrillation pad, and bracelet 600 or bracelet 700.

Figure 8:
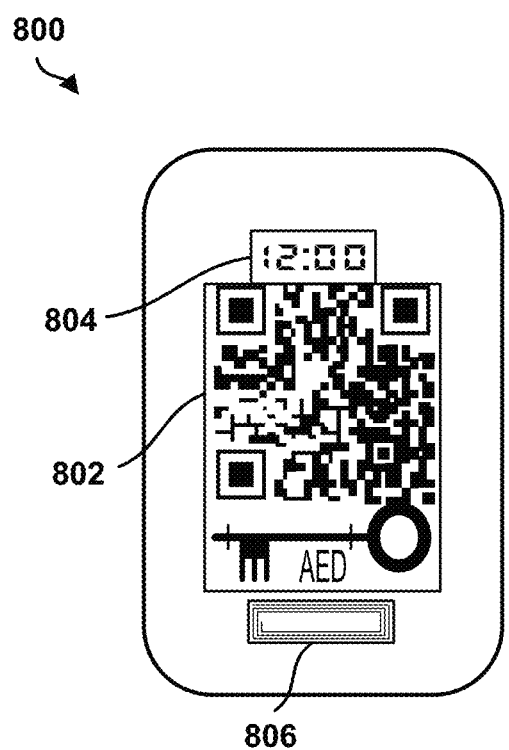
FIG. 8 illustrates an example badge, according to an example implementation.
Figure 9:
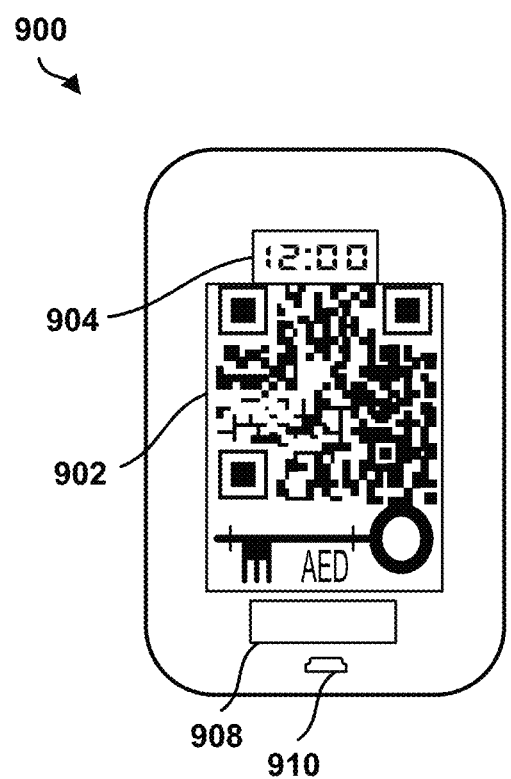
FIG. 9 illustrates another example badge, according to an example implementation.

FIGS. 8 and 9 illustrate example badges 800, 900 that can be included within a disposable cartridge for a defibrillator. As shown in FIG. 8, badge 800 includes a QR code 802, a communication device 804, and a timer 806. In line with the discussion above, communication device 804 can include a NFC chip or an RFID tag. Badge 800 can include an adhesive layer that is covered by a removable backing (not shown). A user can apply badge 800 to a patient by removing the removable backing, and adhering badge 800 to the patient using the adhesive layer.

As shown in FIG. 9, badge 900 similarly includes a QR code 902 and a timer 906. However, unlike badge 800 of FIG. 8, badge 900 includes a memory card 908 and a communication port 910. A computing system, such as computing system 400 of FIG. 5, can read data from memory card 908 by connecting a data cable to communication port 910. Alternatively, a user can remove memory card 908 from badge 900 and insert memory card 908 into a memory card reader of a computing system to read data from memory card 908.

Badge 800 or badge 900 can be packaged within a cartridge for a defibrillator. For instance, a cartridge can include a first defibrillation pad, a second defibrillation pad, and badge 800 or badge 900.

A key can also be associated with a patient's case by using defibrillation pads that are designed with the capability of placing a temporary tattoo on the patient's skin. By way of example, one or both defibrillation pads can be manufactured with ink that is placed on the surface of the defibrillation pad's adhesive gel such that, when applied, the defibrillation pads will leave a QR code imprinted on the patient's skin. Defibrillator 104 can determine the key by reading the QR code with a QR code reader when defibrillator is being prepared for future use. Alternatively, defibrillator 104 can determine the key by accessing configuration information that is programmed for defibrillator 104 prior to use of defibrillator 104. For instance, a user can use a user interface of defibrillator 104 or a defibrillator configuration program accessible to a system administrator to provide the key. The key could be printed on packaging for the disposable cartridge, such that the user could read the key and then program the configuration information. Or a user can insert a memory card into defibrillator 104, with the memory card storing the key, and defibrillator 104 can read the memory card to determine the key. During subsequent patient care, computing system 400 can determine the key by reading the QR code using a QR code reader.

Figure 10:
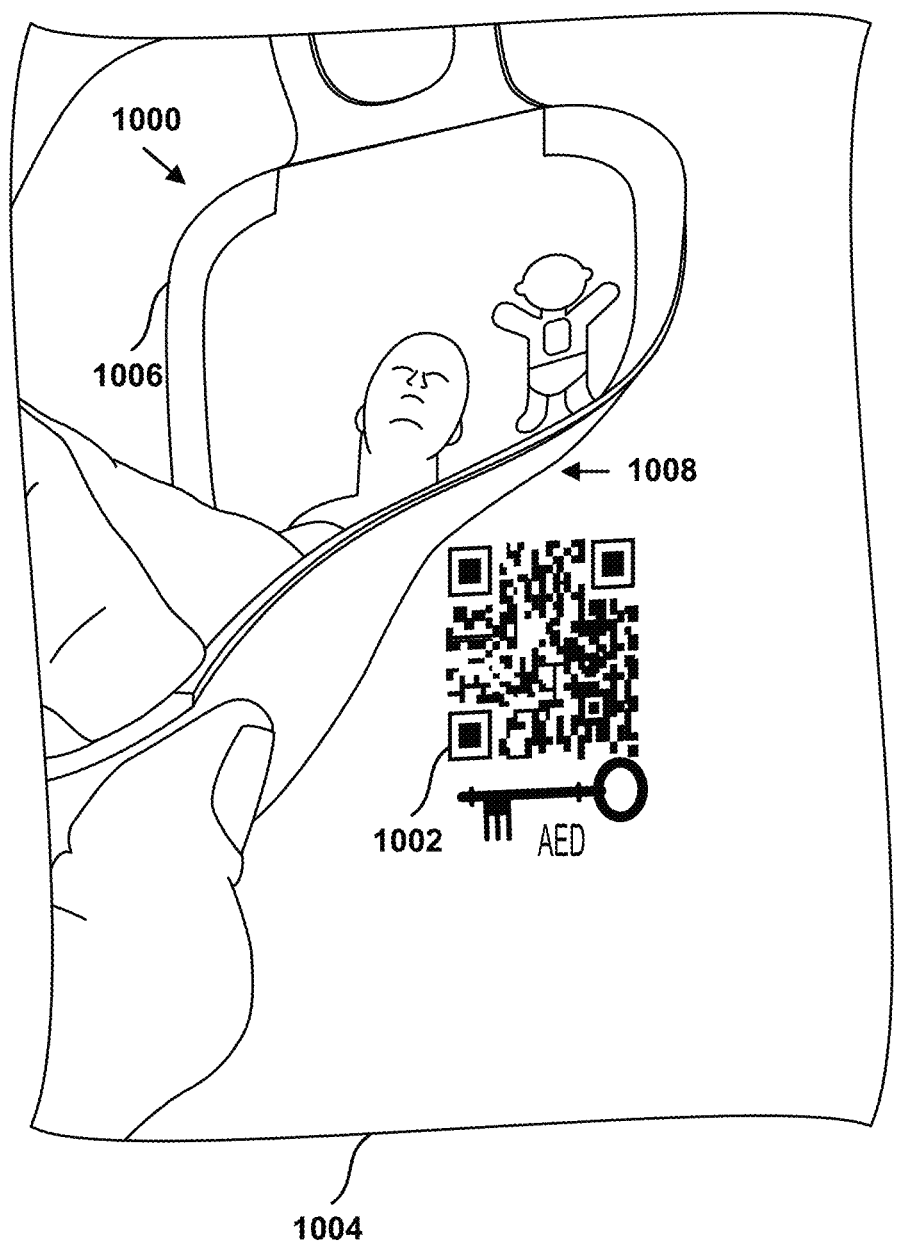
FIG. 10 illustrates an example defibrillation pad, according to an example implementation.

FIG. 10 illustrates an example defibrillation pad 1000. As shown in FIG. 10, defibrillation pad 1000 is designed to imprint an encoded version of a key 1002 on a skin of a patient 1004 when applied. Defibrillation pad 1000 includes a flexible substrate 1006. Defibrillation pad 1000 can further include a removable backing attached to a first side 1008 of flexible substrate 1006 as well as an adhesive gel provided between first side 1008 of flexible substrate 1006 and the removable backing. In addition, a layer of ink can be provided on the adhesive gel such that, when flexible substrate 1006 is applied to patient 1004, the layer of ink imprints encoded version of the key 1002 on the skin of patient 1004. In FIG. 10, encoded version of the key 1002 is a QR code.

In some examples, a defibrillation pad can be designed with the capability of placing a temporary tattoo on the patient's skin only if and when a defibrillation shock is delivered to the patient. By way of example, one or both defibrillation pads can be manufactured with collection of vesicles that contain ink and only rupture and release the ink if exposed to electric current of the large amplitude encountered during a defibrillation shock.

Figure 11:
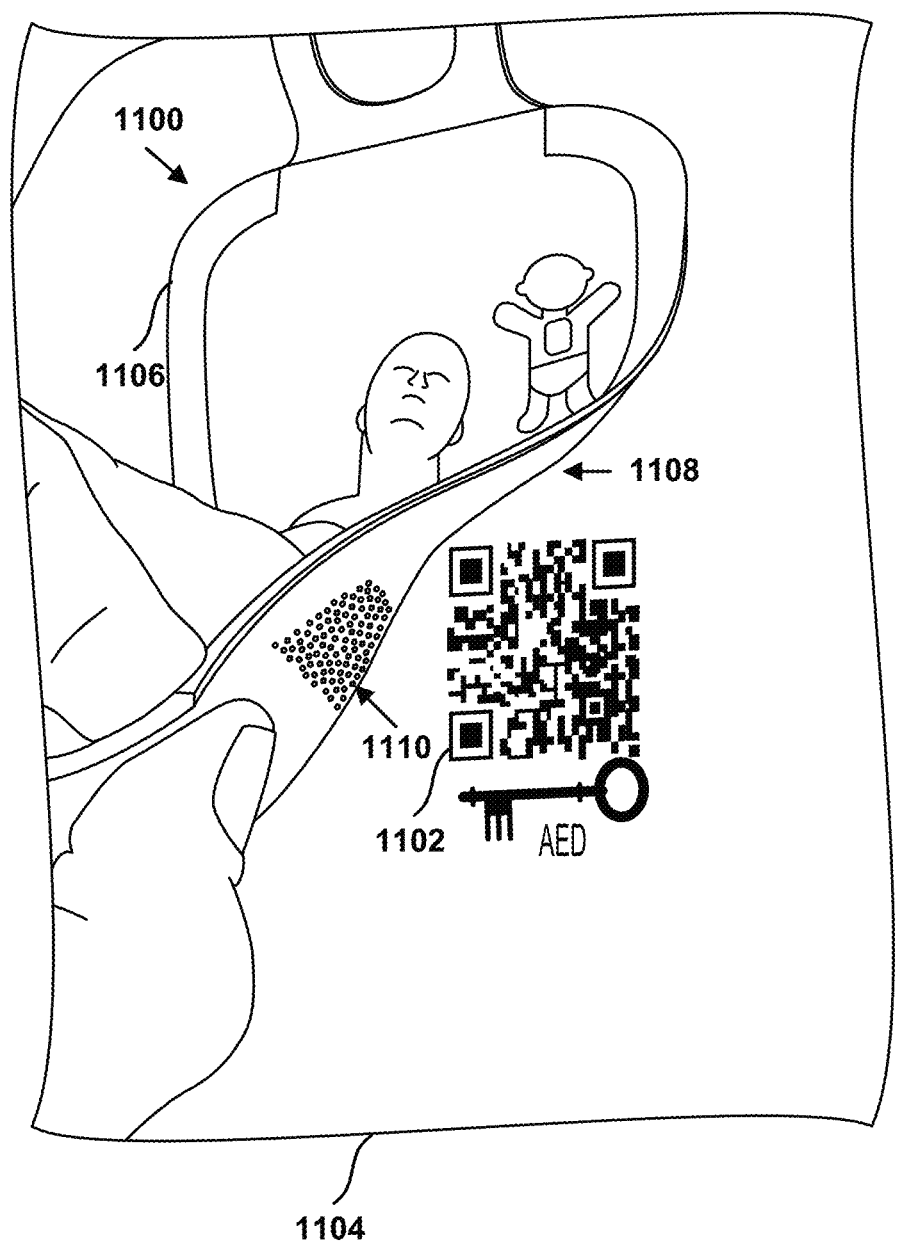
FIG. 11 illustrates another example defibrillation pad, according to an example implementation.

FIG. 11 illustrates an example defibrillation pad 1100. Like defibrillation pad 1000 of FIG. 10, defibrillation pad 1100 is designed to imprint an encoded version of a key 1102 on a skin of a patient 1104 when applied. However, unlike defibrillation pad 1000, defibrillation pad 1100 is designed to imprint the encoded version of the key only if and when a defibrillation shock is applied to the patient. To accomplish this, defibrillation pad 1100 includes a flexible substrate 1106. Defibrillation pad 1100 can further include a removable backing attached to a first side 1108 of flexible substrate 1106 as well as an adhesive gel provided between first side 1108 of flexible substrate 1106 and the removable backing. In addition, a collection of vesicles 1110 is be provided on the adhesive gel. Collection of vesicles 1110 include ink and are configured to rupture when an electric current of sufficient amplitude (e.g., an amplitude that is greater than or equal to the amplitude encountered during a defibrillation shock) is applied to defibrillation pad 1100. Upon rupturing, the ink within collection of vesicles 1110 imprints encoded version of the key 1102 on the skin of patient 1104. In FIG. 11, encoded version of the key 1102 is a QR code.

In other examples, a defibrillator can obtain a key using a fingerprint scanner or a retinal scanner. At some point during the patient care event, a user can scan a fingerprint of the patient or obtain a retina image from the patient. The fingerprint or retina image can then serve as the key. For instance, during subsequent patient care, computing system 400 can obtain the fingerprint or retina image, and use the fingerprint or retina image to access the event data from server 502.

Similarly, in some examples, a defibrillator can obtain a key by obtaining an image of an identification card (e.g., a driver's license or a passport). During subsequent patient care, computing system 400 can obtain an image of the same identification card, and use the image to access the event data from server 502.

Figure 12:
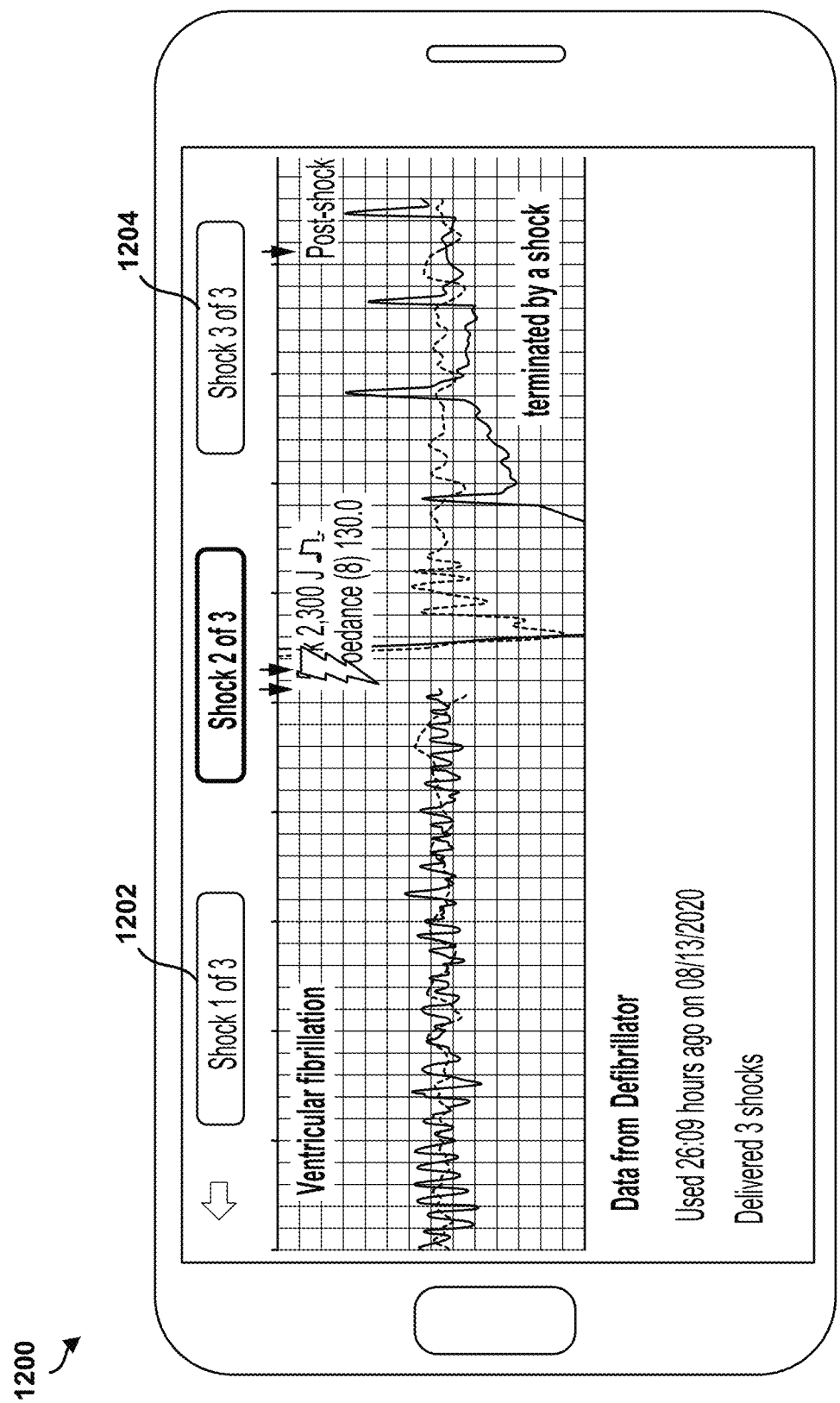
FIG. 12 illustrates example event data, according to an example implementation.

FIG. 12 illustrates example event data 1200 that can be displayed on a computing system, such as computing system 400 of FIG. 5. As shown in FIG. 12, event data 1200 includes physiologic monitoring data obtained using a sensor of a defibrillator. Event data 1200 includes a few seconds of ECG data surrounding delivery of a shock. In the example of FIG. 12, event data 1200 corresponds to a second shock from among three shocks that were delivered to a patient during a patient care event. A medical professional can view ECG data surrounding the other two shocks using user interface elements 1202, 1204. Event data 1200 is also labeled with an indication of a detected rhythm, namely, ventricular fibrillation. Further, event data 1200 indicates an energy level of the shock. Still further, event data 1200 includes a timestamp indicative of when the defibrillator was used. The displayed ECG data can include ECG data obtained while CPR was not being performed on the patient (e.g., during a pause in CPR).

FIG. 13 shows a flowchart of an example of a method 1300 performed by a defibrillator. Method 1300 shown in FIG. 13 presents an example of a method that could be performed by a defibrillator, such as the AED 200 shown in FIG. 2 or the monitor defibrillator 300 shown in FIG. 3, for example. Further, devices or systems may be used or configured to perform logical functions presented in FIG. 13. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 1300 may include one or more operations, functions, or actions as illustrated by one or more of blocks 1302-1308. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 8, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 1302, method 1300 includes obtaining, by a defibrillator, event data regarding treatment provided to a patient. The treatment is provided to the patient while the defibrillator is attached to the patient. The event data can include physiologic monitoring data obtained using a sensor of the defibrillator, such as ECG data. Further, the ECG data can include ECG data obtained before any shocks are delivered to the patient by the defibrillator and/or ECG data obtained while CPR is not being performed on the patient. The event data can also include audio data or video data.

In addition, obtaining the event data can involve obtaining physiologic monitoring data using a sensor of the defibrillator, and then analyzing the physiologic monitoring data so as to obtain the event data. For instance, the defibrillator can determine an AMSA using ECG data.

At block 1304, method 1300 includes obtaining, by the defibrillator, a key that facilitates validating a request from a computing device to access the event data. In one example, obtaining the key can involve generating a number using a processor of the defibrillator. In other examples, obtaining the key can involve reading the key from an RFID tag, reading a QR code using a QR code reader, or reading the key from an NFC chip using an NFC device. The RFID tag, QR code, or NFC chip can be provided on a bracelet or a badge. In still other examples, obtaining the key can involve obtaining an image of a fingerprint of the patient using a fingerprint scanner, obtaining a retina image from the patient using a retinal scanner, or obtaining an image of an identification card of the patient using a camera.

At block 1306, method 1300 includes associating, by the defibrillator, the key with the event data. For instance, after obtaining the key, the defibrillator can store the key and the event data together within an event data file. Further, at block 1308, method 1300 includes transmitting, by the defibrillator, the key and the event data to a server in a network for storage. For instance, the defibrillator can transmit an event data file including the key and the event data to the server.

In some examples, method 1300 also includes writing the key on an NFC chip or a removable memory card. For instance, after generating a number, the defibrillator can write the key on an NFC chip or a removable memory card. Further, the writing of the key can occur based on determining that defibrillation pads are attached to the patient.

In examples in which the key is stored in a removable memory card, the defibrillator can prompt an operator to attach the removable memory card to the patient. For instance, the defibrillator can provide voice prompts that instruct the operator to attach the removable memory card to the patient.

Similarly, in examples in which the key is provided on or stored on a bracelet or badge, method 1300 can also include prompting an operator to attach the bracelet or badge to the patient. For instance, the defibrillator can provide voice prompts that instruct the operator to attach the bracelet or badge to the patient.

FIG. 14 shows a flowchart of an example of a method performed by a computing system. Method 1400 shown in FIG. 14 presents an example of a method that could be performed by computing system 400 of FIGS. 4 and 5, for example. Further, devices or systems may be used or configured to perform logical functions presented in FIG. 14.

At block 1402, method 1400 includes obtaining, using a computing system, a key associated with event data regarding treatment provided to a patient using a defibrillator. The treatment is provided to the patient while a defibrillator is attached to the patient.

In some examples, obtaining the key can involve reading the key from an NFC chip, an RFID tag, or a QR code. The NFC chip, RFID tag, or QR code can be provided on a bracelet or a badge that is attached to the patient. Alternatively, the QR code can be provided on a temporary tattoo. Further, in some examples, obtaining the key can involve obtaining a fingerprint, obtaining a retinal image, or obtaining an image of an identification card. Still further, obtaining the key can involve reading the key from a removable memory card.

At block 1404, method 1400 includes transmitting, by the computing system, the key to a server in a network. At block 1406, method 1400 includes responsive to transmitting the key to the server, receiving, by the computing system from the server, the event data associated with the key. And at block 1408, method 1400 includes displaying, by the computing system, a portion of the event data.

The event data can include physiologic monitoring data obtained using a sensor of the defibrillator, such as ECG data. Further, the ECG data can include ECG data obtained before any shocks are delivered to the patient by the defibrillator and/or ECG data obtained while CPR is not being performed on the patient. The event data can also include audio data or video data.

Figure 15:
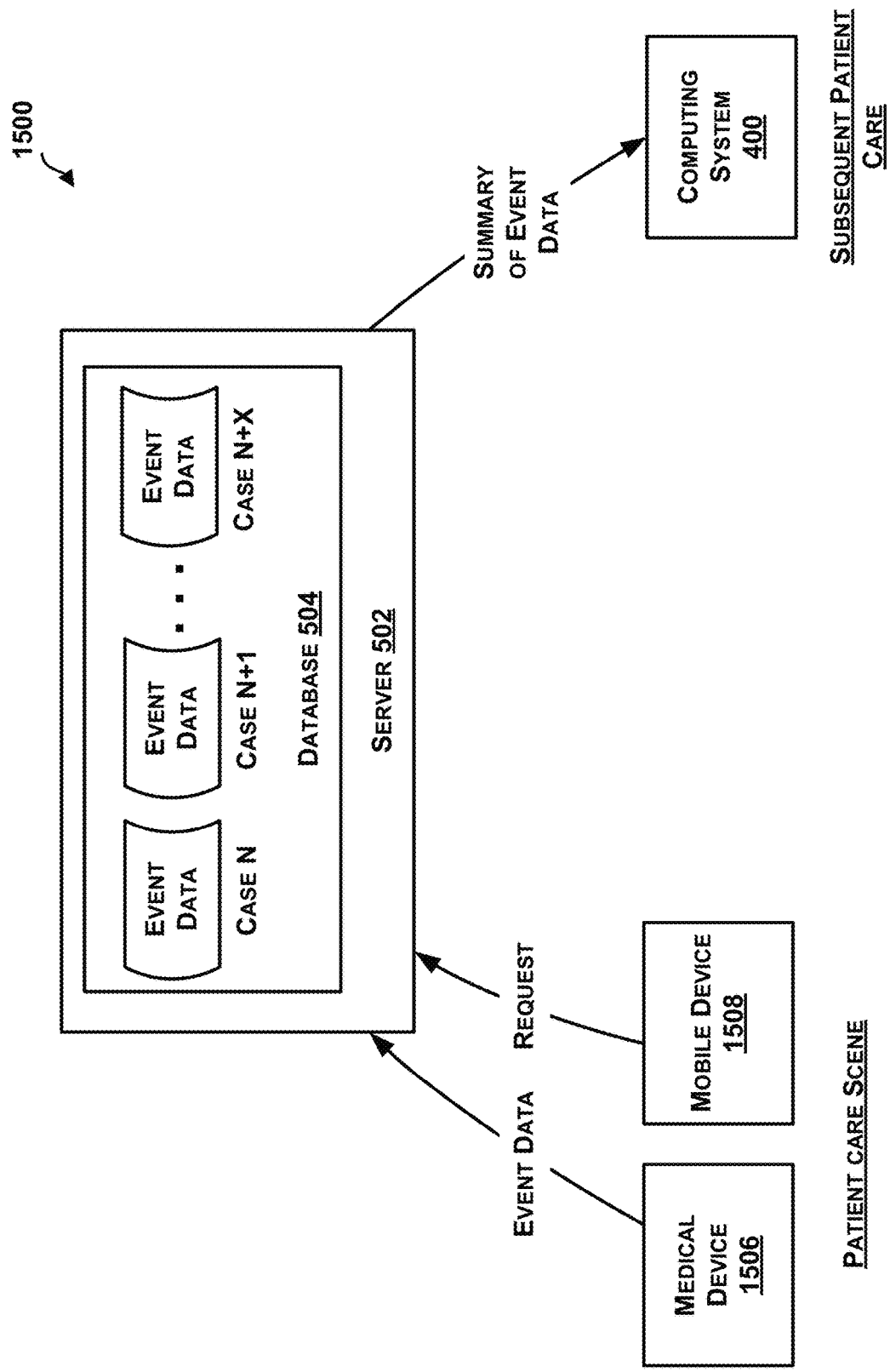
FIG. 15 illustrates another example system, according to an example implementation.

FIG. 15 illustrates an example system 1500. In line with the discussion above, system 1500 allows a summary of event data regarding treatment provided to a patient to be transmitted to a selected recipient for the event data. Like system 500 of FIG. 5, system 1500 includes computing system 400 as well as server 502. Server 502, in turn, includes database 504 storing event data for individual cases. Event data for individual cases is received from medical devices, such as medical device 1506.

System 1500 also includes a mobile device 1508. Mobile device 1508 can cause a summary of the event data obtained by medical device 1506 to be transmitted to the selected recipient by transmitting to server 502 a request, with the request including an indication of the recipient and identifier of medical device 1506 or an encoded version of the identifier. Reception of the request by server 502 can then cause server 502 to generate the summary of the event data and transmit the summary of the event data to the recipient. For instance, server 502 can transmit the summary of the event data to computing system 400. Computing system 400 can include a computing system that recipient uses to access email communications, or a dedicated computing system that is located at a medical provider and connected to a medical alert system.

Medical device 1506 can include any type of pre-hospital device (e.g., advanced life support device or accessory), emergency response device (e.g., basic life support device or accessory), or public access devices (e.g., an AED or AED accessory). Examples of medical devices include a defibrillator, monitor defibrillator, PAD AED, chest compression system, CPR coaching device, or laryngoscope.

During a patient care event, at the end of a patient care event, or at a later time when medical device 1506 establishes a connection to server 502, medical device 1506 transmits event data to server 502. Server 502 then stores the event data in database 504. Server 502 stores the event data in a manner that allows for subsequently accessing the event data using an identifier of medical device 1506.

In some examples, server 502 can apply analytics to the event data to derive useful summary information from the event data. For instance, the summary information can include a detected rhythm(s) or AMSA determined using ECG data, for instance. The summary information can also include a segment of ECG data that is annotated as being ECG data that corresponds to a time when CPR was not being performed.

Mobile device 1508 can take the form of a smartphone, tablet, or wearable computing device, for instance. Mobile device 1508 can obtain an encoded version of an identifier of medical device 1506, obtain a selection of a recipient for the event data, and cause server 502 to transmit a summary of the event data to the recipient. By way of example, an application on mobile device 1508 can instruct a user to read a QR code using mobile device 1508. The QR code can be provided on a label that is attached to medical device 1506, displayed on a display of medical device 1506, or printed on a piece of paper by medical device 1506, for instance. After reading the QR code, the application on mobile device 1508 can prompt the user to select a recipient for the event data. After receiving a selection of the recipient, mobile device 1508 can transmit a request to server 502. The request can include the recipient and either the encoded version of the identifier of medical device 1506 or the identifier of medical device 1506.

In some examples, mobile device 1508 can display a list of recipients. Mobile device 1508 can populate the list based on medical providers (e.g., hospitals) that are located within a threshold distance of a location of medical device 1508. Alternatively, mobile device 1508 can populate the list based on configuration information previously configured by the user or a system administer. The list can display one or more physical addresses (e.g., street number and name and/or city) or names (e.g., hospital department and name). Mobile device 1508 can associate the physical addresses and names with email addresses or device names. Medical device 1508 can also prompt the user to select a recipient by inputting an address for the recipient (e.g., an email address or a name of a device that is connected to a medical alert system).

In some examples, mobile device 1508 can send the request to server 502 before the patient care event is completed. With this approach, server 502 can send a summary of event data to the recipient after server 502 receives the event data. Alternatively, the request can designate a time or multiple times for summaries of event data to be sent (e.g., at the end of the patient care event or after expiration of a given period of time (e.g., thirty minutes).

In some examples, the application on mobile device 1508 can allow the user to provide additional information, such as text, images, or videos. Server 502 can then add the additional information to the summary of the event data that is transmitted to the recipient. Further, the application on mobile device 1508 can require the user to login to an account before allowing the user to use the application.

In alternative method of operation, the application on mobile device 1508 might not require a user to select a recipient for the event data. Instead, mobile device 1508 can be configured to automatically cause a summary of the event data to be transmitted to devices that are registered with a medical alert system and within a threshold distance of a location of mobile device 1508. The automatic transmission can occur after the application on mobile device 1508 obtains the image of the encoded version of the identifier of medical device 1506.

Further, mobile device 1508 can be configured to obtain and store device data indicative of properties of medical device 1506. For instance, mobile device 1508 can obtain from server 502 device data that is indicative of a serial number, battery level, or expiration date for medical device 1506 or an accessory of medical device 1506. After a patient care event, a user can re-visit the device data to review properties of medical device 1506. For privacy/security reasons, the device data does not include any patient-related information.

Mobile device 1508 can also determine a location of mobile device 1508, and send the location or information derived from the location to server 502 for inclusion in the summary of event data. For instance, mobile device 1508 can determine a travel time from the location of mobile device 1508 to a location of the recipient, and send the travel time to server 502. Server 502 can then include the travel time in the summary of the event data. Alternatively, server 502 can determine the travel time using the location of the mobile device and the location of the recipient.

The summary of event data can take the form of a portable document format (PDF) file. For instance, server 502 can generate the summary of event data by inserting portions of the event data into different fields of the PDF file. The summary of the event data can include one or more of ECG data, impedance values, an initial detected rhythm, number of shocks, SpO2, CO2, CPR depth, or CPR rate, for example. Server 502 can identify the appropriate event data using the identifier of medical device 1506 or the encoded version of the identifier of medical device 1506. When the identifier is encoded, server 502 can decode the identifier to determine the identifier. In some examples, server 502 can also use a timestamp associated with a request to identify the appropriate event data. The timestamp can allow the server 502 to distinguish between two sets of event data that are associated with the same medical device but correspond to different patient care events, such as patient care events occurring on different days.

Figure 16:
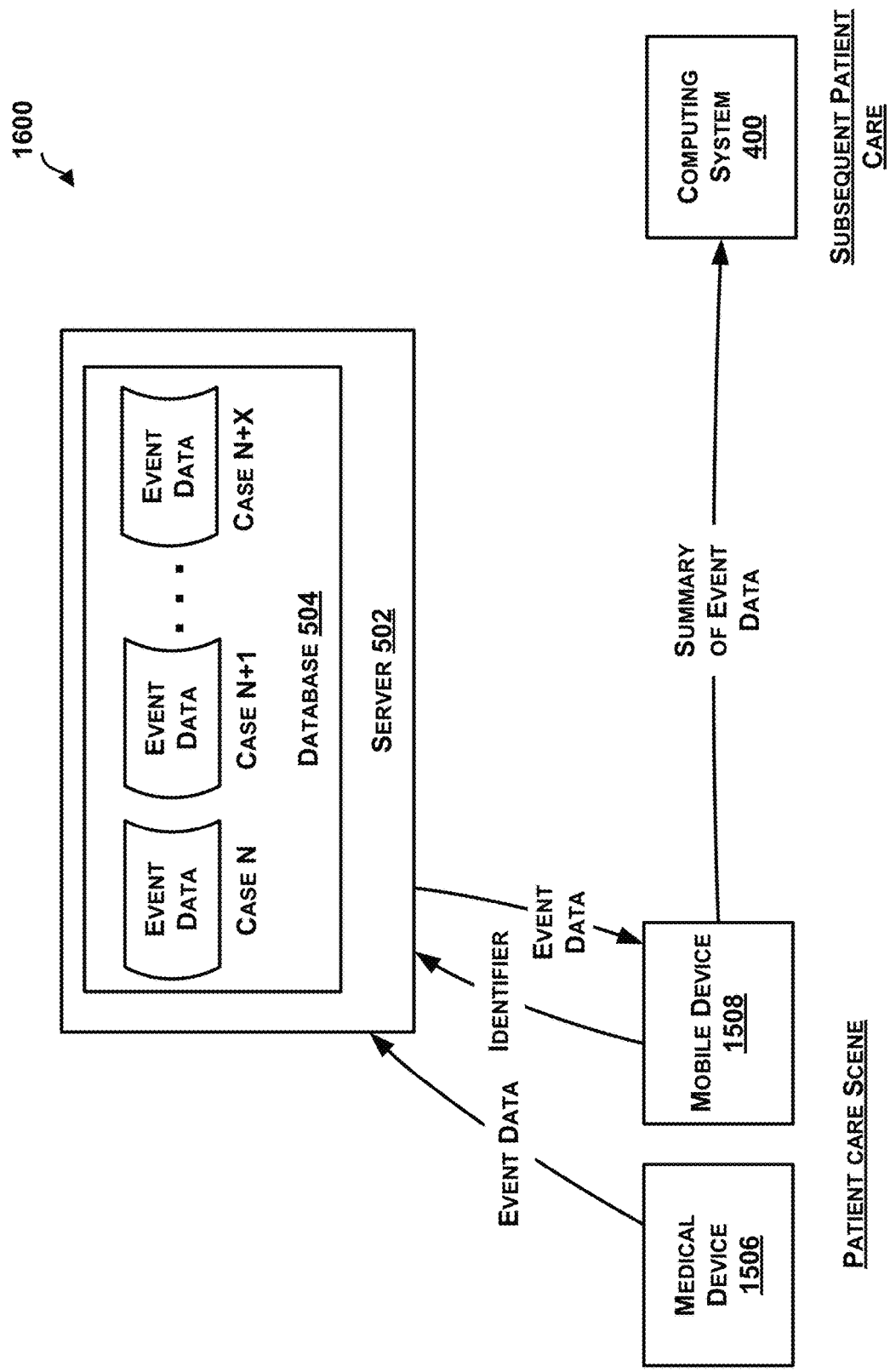
FIG. 16 illustrates another example system, according to an example implementation.

FIG. 16 illustrates an example system 1600. System 1600 allows mobile device 1508 to transmit a summary of event data regarding treatment provided to a patient to a selected recipient for the event data. Like system 1500 of FIG. 15, system 1600 includes server 502, computing system 400, medical device 1506, and mobile device 1508. System 1600 differs from system 1500 in that mobile device uses the identifier of medical device 1506 to obtain event data gathered by medical device 1506, and then generates the summary of event data and transmits the summary of the event data to the recipient. For instance, after obtaining the encoded version of the identifier of medical device 1506, mobile device 1508 decodes the encoded version of the identifier so as to obtain the identifier. Mobile device 1508 then transmits a request to server 502, with the request including identifier, and receives the event data. Further, mobile device generates a summary of the event data, and transmits the summary of the event data to the recipient. Like in system 1500, generating the summary of the event data can involve preparing a PDF file using portions of the event data.

Figure 17:
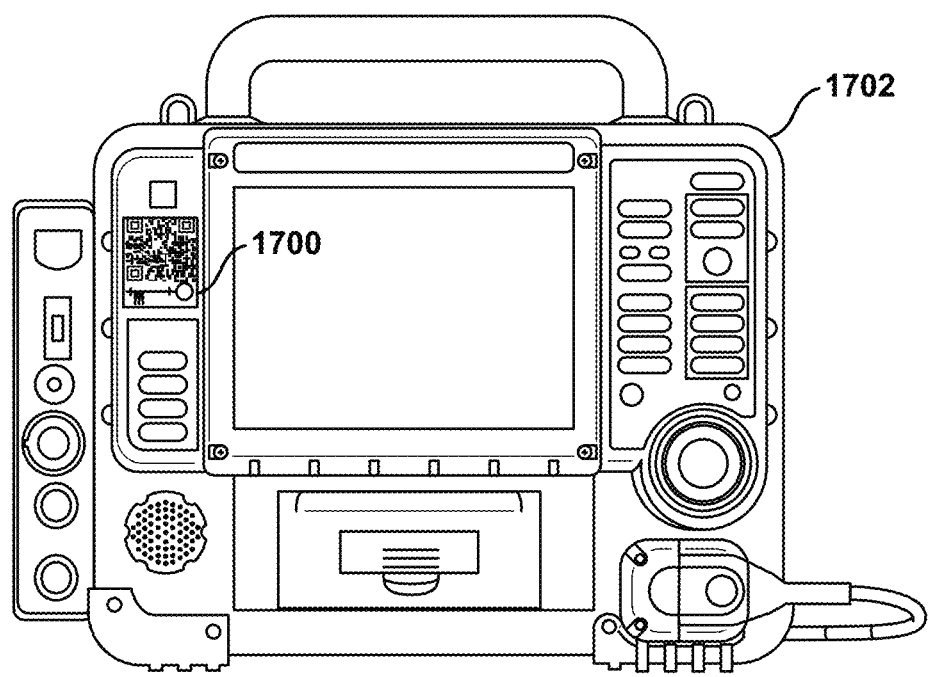
FIG. 17 illustrates an example encoded version of an identifier of a medical device, according to an example implementation.

FIG. 17 illustrates an example encoded version of an identifier 1700 of a medical device 1702. As shown in FIG. 17, encoded version of the identifier 1700 is a QR code. The QR code is provided on a label that is attached to a housing of medical device 1702.

Figure 18:
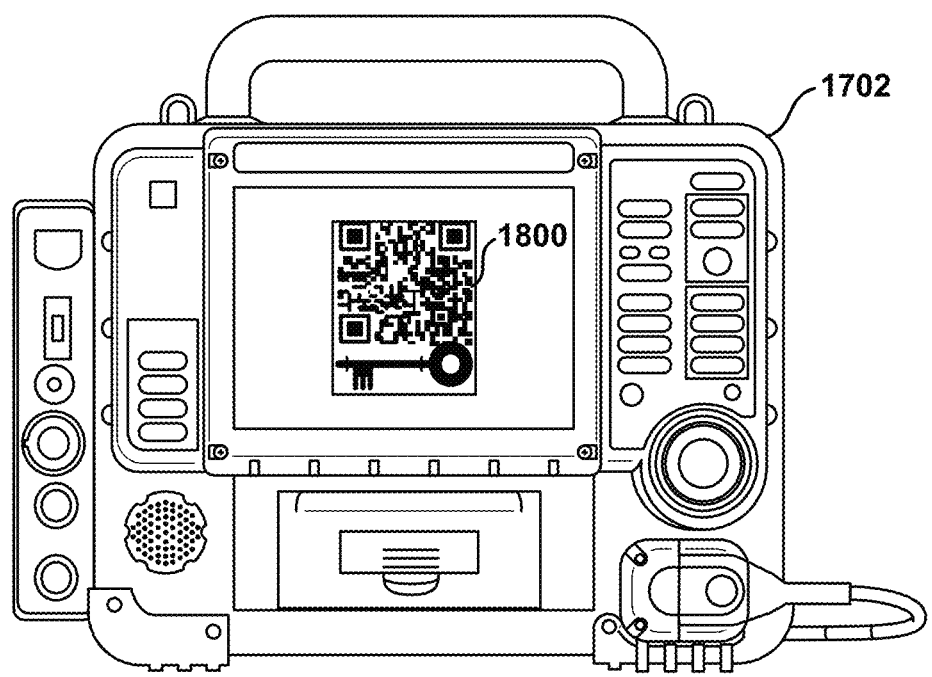
FIG. 18 illustrates another example encoded version of an identifier of a medical device, according to an example implementation.

FIG. 18 illustrates another example encoded version of an identifier 1800 of medical device 1702. As shown in FIG. 18, encoded version of the identifier 1800 is also a QR code. However, in FIG. 17, in FIG. 18, the QR code is displayed on a display of medical device 1802. This allows for generation of QR codes that change over time. With this approach, each individual case for which medical device 1702 obtains event data can have a unique QR code.

Figure 19:
FIG. 19 shows a flowchart of an example of a method performed by a mobile device, according to an example implementation.

FIG. 19 shows a flowchart of an example of a method performed by a mobile device, according to an example implementation. Method 1900 shown in FIG. 19 presents an example of a method that could be performed by mobile device 1508 of FIGS. 15 and 16, for example. Further, devices or systems may be used or configured to perform logical functions presented in FIG. 19.

At block 1902, method 1900 includes obtaining, by a mobile device, an encoded version of an identifier of a medical device. The medical device is configured to obtain event data regarding treatment provided to a patient, and to transmit the event data to a server.

The encoded version of the identifier can be provided on a label that is attached to the medical device. Alternatively, the encoded version of the identifier can be displayed by a display of the medical device or printed on a piece of paper by the medical device. In some examples, obtaining the encoded version of the identifier involves reading a QR code using a QR code reader.

The event data can include physiologic monitoring data obtained using a sensor of the defibrillator, such as ECG data. Further, the ECG data can include ECG data obtained before any shocks are delivered to the patient by the defibrillator and/or ECG data obtained while CPR is not being performed on the patient. The event data can also include audio data or video data.

At block 1904, method 1900 includes obtaining, by the mobile device, a selection of a recipient for the event data. The recipient can include an email address associated with a medical provider. Alternatively, the recipient can include a device that is located at a medical provider and connected to a medical alert system. In some examples, obtaining the selection of the recipient can involve obtaining a selection of the recipient from among a list of recipients displayed by the mobile device.

At block 1906, method 1900 includes causing, by the mobile device, a summary of the event data to be transmitted to the recipient. The summary of the event data can include a PDF file. In one example, causing the summary of the event data to be transmitted to the recipient involves: decoding the encoded version of the identifier of the medical device so as to obtain the identifier of the medical device, and transmitting to a server a request that includes: an indication of the recipient and the identifier of the medical device. Receipt of the request by the server then causes the server to generate the summary of the event data to the recipient.

In another example, causing the summary of the event data to be transmitted to the recipient involves transmitting to a server a request that includes: an indication of the recipient and the encoded version of the identifier of the medical device. Receipt of the request by the server then causes the server to generate the summary of the event data to the recipient.

In yet another example, causing the summary of the event data to be transmitted to the recipient involves: decoding the encoded version of the identifier of the medical device so as to obtain the identifier of the medical device, obtaining the event data from a server using the identifier of the medical device, generating the summary of the event data, and transmitting the summary of the event data to the recipient.

In some examples, the event data can include device data indicative of properties of the medical device. Method 1900 can then involve storing the device data on the mobile device.

Method 1900 can also include determining a location of the mobile device. Further, the summary of the event data can include an indication of a travel time from the location of the mobile device to a location of the recipient, or an indication of the location of the mobile device.

The systems and methods described herein are very beneficial for providing better patient care after a cardiac event. Information gathered by a defibrillator can provide unique, valuable insight into the cause of a cardiac event. That information can be beneficial to a physician in a hospital, minutes to hours later, when she is selecting the appropriate course of care for that patient. For example, if the physician does not know that the patient had VF and was defibrillated in the field, the patient might be discharged from the hospital without adequate measures to prevent or treat another episode of VF.

Further, the systems and methods described herein provide efficient ways to provide data gathered by a medical device to a recipient, such as a medical professional that will provide subsequent care for the patient. Providing this data to the recipient allows the recipient to provide better care and proper preparation for an incoming patient.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A defibrillator comprising:
 a first defibrillation pad;
 a second defibrillation pad;
 a processor configured to:
  detect that the first defibrillation pad and the second defibrillation pad are attached to a patient; and
  generate a key in response to detecting the first defibrillation pad and the second defibrillation pad are attached to the patient; and
 a bracelet comprising a memory, the memory configured to store the key generated by the defibrillator in response to detecting the first defibrillation pad and the second defibrillation pad are attached to the patient, wherein the key facilitates validating a request from a computing system to access event data, wherein the event data relates to treatment provided to the patient while the defibrillator is attached to the patient.

2. The defibrillator of claim 1, wherein the bracelet further comprises a near-field communication (NFC) chip, and wherein the memory is a memory of the NFC chip.

3. The defibrillator of claim 1, wherein the bracelet further comprises a radio-frequency identification (RFID) tag, and wherein the memory is a memory of the RFID tag.

4. The defibrillator of claim 1, wherein the bracelet further comprises a display configured to display a timer that is indicative of a time that the treatment is provided to the patient.

5. The defibrillator of claim 4, wherein the timer is indicative of a time that the bracelet is removed from a cartridge.

6. The defibrillator of claim 4, wherein the timer is indicative of a time that the defibrillator is powered on.

7. The defibrillator of claim 1, further comprising a communication port that facilitates transferring data between the memory and the defibrillator or another computing system.

8. The defibrillator of claim 1, wherein the memory comprises a removable memory card.

9. The defibrillator of claim 8, wherein the removable memory card is unable to be removed while the bracelet is being worn by the patient.

10. The defibrillator of claim 1, further comprising a quick response (QR) code that encodes the key.

11. The defibrillator of claim 10, wherein the QR code is provided on packaging for a cartridge.

12. The defibrillator of claim 10, wherein the QR code is provided on the bracelet.

13. The defibrillator of claim 1, wherein the first defibrillation pad comprises:
   a flexible substrate;
   a removable backing attached to a first side of the flexible substrate;
   an adhesive gel provided between the first side of the flexible substrate and the removable backing; and
   a layer of ink provided on the adhesive gel such that, when the removable backing is removed and the flexible substrate is applied to the patient, the layer of ink imprints an encoded version of the key on a skin of the patient.

14. The defibrillator of claim 1, wherein the first defibrillation pad comprises:
   a flexible substrate;
   a removable backing attached to a first side of the flexible substrate;
   an adhesive gel provided between the first side of the flexible substrate and the removable backing; and
   a collection of vesicles provided on the adhesive gel,
   wherein vesicles of the collection of vesicles comprise ink and are configured to rupture when an electric current is applied to the defibrillation pad.

15. The defibrillator of claim 14, wherein the collection of vesicles are configured to rupture when an electric current having an amplitude that satisfies a threshold condition is applied to the defibrillation pad.

16. The defibrillator of claim 1, wherein the key is a randomly generated number.

17. The defibrillator of claim 1, wherein, to detect whether the first defibrillation pad and the second defibrillation pad are attached to the patient, the processor is configured to sense an impedance using a first sensor on the first defibrillation pad and a second sensor on the second defibrillation pad.

18. The defibrillator of claim 1, wherein the processor is further configured to:
   detect that the first defibrillation pad and the second defibrillation pad are detached from the patient after generation of the key; and
   generate voice prompts that instruct an operator to remove the bracelet in response to detecting that the first defibrillation pad and the second defibrillation pad are detached from the patient.

19. The defibrillator of claim 1, wherein the processor is further configured to:
   detect that the first defibrillation pad and the second defibrillation pad are disconnected from the defibrillator after generation of the key; and
   generate voice prompts that instruct an operator to remove the bracelet in response to detecting that the first defibrillation pad and the second defibrillation pad are disconnected from the defibrillator.

* * * * *